United States Patent [19]

Sundblom et al.

[11] Patent Number: 4,758,238

[45] Date of Patent: Jul. 19, 1988

[54] FAST RESPONSE TUBELESS VACUUM ASPIRATION COLLECTION CASSETTE

[75] Inventors: Leif J. Sundblom, Castro Valley; William T. George, Oakland, both of Calif.

[73] Assignee: Alcon Laboratories, Inc., Fort Worth, Tex.

[21] Appl. No.: 83,904

[22] Filed: Aug. 6, 1987

Related U.S. Application Data

[63] Continuation of Ser. No. 907,589, Sep. 18, 1986, abandoned, which is a continuation-in-part of Ser. No. 780,073, Sep. 25, 1985, abandoned.

[51] Int. Cl.$^4$ .............................................. A61M 1/00
[52] U.S. Cl. .................................... 604/319; 604/321; 604/153
[58] Field of Search ............... 604/19, 22, 35, 48, 604/51, 68, 93, 118, 119, 120, 128–129, 151–153, 246–247, 902, 317, 319, 320–321, 324, 403; 119/14.46

[56] References Cited

U.S. PATENT DOCUMENTS

| | | | |
|---|---|---|---|
| 2,211,167 | 8/1940 | Safford | 251/131 |
| 3,019,815 | 2/1962 | Lenardon et al. | 137/612.1 |
| 3,269,410 | 8/1966 | Alvarado . | |
| 3,515,169 | 6/1970 | Berg et al. . | |
| 3,613,729 | 10/1971 | Dora | 137/624 |
| 3,666,230 | 5/1972 | Pauliukonis . | |
| 3,850,265 | 11/1974 | Blower et al. . | |
| 4,064,630 | 12/1977 | Killick | 32/22 |
| 4,064,639 | 12/1977 | Killick | 32/22 |
| 4,121,584 | 10/1978 | Turner et al. . | |
| 4,142,523 | 3/1979 | Stegeman . | |
| 4,144,644 | 3/1979 | Olsen | 32/22 |
| 4,223,813 | 9/1980 | Garrett et al. | 222/447 |
| 4,236,880 | 12/1980 | Archibald | 417/478 |
| 4,324,243 | 4/1982 | Helfgott et al. | 128/276 |
| 4,475,904 | 10/1984 | Wang | 604/119 |
| 4,479,760 | 10/1984 | Bilstad et al. | 417/395 |
| 4,493,695 | 1/1985 | Cook | 604/27 |

*Primary Examiner*—C. Fred. Rosenbaum
*Assistant Examiner*—Gene B. Kartchner
*Attorney, Agent, or Firm*—Zarley, McKee, Thomte, Voorhees & Sease

[57] ABSTRACT

A fast response, tubeless vacuum aspiration collection cassette includes large and small containers defined within a cassette housing adapted to be removably secured to a surgical aspiration machine. A first wall of the cassette housing abutting the machine includes connectors thereto to provide a controlled variable vacuum level to the small container, and a fixed vacuum level to the large container. Valves formed in the first wall are interconnected by flow channels therein extending to the containers, each valve having an actuating stem extending from the wall to be actuated selectively by the machine. A second wall opposed to the first wall includes a connector extending to a surgical probe or cutting instrument. The channels and valves are arranged so that when the containers are isolated by a first valve, the controlled vacuum level may be applied to the surgical probe through a second valve connecting it to the small ontainer volume. Whenever the controlled vacuum is shut off to the probe by the second valve, the first valve is opened to permit the fixed vacuum in the larger container to be applied to the smaller container to transfer aspirant fluid therein to the larger container. The cassette also can have a fluid infusion input and output. Flow channels and a valve in the first wall of the cassette housing can control flow of infusion fluid from an infusion fluid source to an infusion fluid tool.

11 Claims, 9 Drawing Sheets

FIG_1

FIG_2

FIG_3

FIG_4

FIG_5  FIG_6  FIG_7

FIG_8

FAST RESPONSE TUBELESS VACUUM ASPIRATION COLLECTION CASSETTE

REFERENCE TO RELATED APPLICATION

This is a continuation of co-pending application Ser. No. 907,589 filed on Sept. 18, 1986 now abandoned, which is a continuation-in-part application from previous filed and co-pending U.S. application Ser. No. 780,073, filed Sept. 25, 1985, now abandoned.

BACKGROUND OF THE INVENTION

In modern surgical practice, many procedures which formerly required large incisions have been supplanted by techniques employing microsurgical tools. Such tools are generally introduced to the surgical site through small incisions which create far less surgical trauma, and hasten healing and recovery.

A significant aspect of many of the newly developed surgical tools is the use of vacuum aspiration to draw tissue into a power driven cutting head. It is well recognized that the rate of tissue cutting and removal is related to the rate of operation of the cutting head, and also to the vacuum level applied to the aspiration port associated with the cutting head. Thus it is clear that precise control of the vacuum level is essential to successful operation of this type of surgical instrument.

Until recently it was standard practice to have tubing and hoses extending to the cutting instrument to provide aspiration, irrigation fluid, and motive power to the cutting head. The tubing generally was manually secured through pinch valves on the console of a surgical instrument control machine to provide control of the irrigation and aspiration functions. However, this procedure was subject to human error in the placement of the proper tubing in the proper pinch valve, and it was also possible for the tubing to become dislodged accidentally. The outcome of such errors can be catastrophic during surgery.

One means for overcoming this problem is disclosed in U.S. Pat. No. 4,475,904, issued Oct. 9, 1984 to Carl C. T. Wang. This device provided a pair of aspiration containers in a cassette housing, one container having a significantly smaller volume than the other. The containers are connected by tubing affixed to an outer wall of the cassette, and valves extending from the console of the surgical control machine are disposed to engage the tubing automatically when the cassette is secured to the machine. Also, the vacuum connections to the cassette are engaged automatically upon installation of the cassette. Thus the human error aspect is alleviated. More significantly, the assembly provides the fast response to changes in vacuum associated with a small volume while also providing a large storage capacity.

However, pinch valves mounted on the exterior of a machine exhibit intrinsic reliability problems, such as clogging by foreign matter, sticking, and the like. Furthermore, the tubing itself must be extremely resilient to expand quickly when the pinch valves open, so that the response time of the overall assembly does not lag. If a tubing section remains pinched by a valve for a long period of time, plastic deformation may occur, and the flow channel will be constricted, thus altering the operating characteristics of the surgical tool. Temperature changes may also affect the resilience of the tubing.

It is additionally problematic that many times surgery requires contemporary use of different types of surgical instruments. As previously discussed, aspiration, irrigation, and mode of power for a cutting tool require connection to different sources. Use of tubing or hoses is susceptible to problems, as previously discussed, which is compounded by the different sources and types of tools. It would therefore be advantageous to have an integrated control center and conduit for the different sources and tools.

SUMMARY OF THE PRESENT INVENTION

The present invention generally comprises a vacuum aspiration collection system which features all of the conveniences and error-free aspects of a cassette system, while alleviating the problems associated with tubing and pinch valve operation. Thus the invention provides fast response to changes in demand for vacuum at the aspiration port, large capacity for storage of aspirated fluids and tissue, and highly reliable setup and operation.

In a first preferred embodiment of the invention, the fast response, tubeless vacuum aspiration collection cassette includes large and small containers defined within a cassette housing adapted to be removably secured to a surgical aspiration machine. A first wall assembly of the cassette housing abutting the machine includes connectors positioned to engage ports in the machine to provide a controlled variable vacuum level to the small container, and a fixed vacuum level to the large container. Valves formed in the first wall are interconnected by flow channels therein extending to the containers, each valve having an actuating stem extending from the wall and positioned to be actuated selectively by appropriate components of the machine.

A second wall of the cassette housing opposed to the first wall includes a tubing connector extending to a surgical probe or cutting instrument. The channels and valves are arranged so that when the containers are isolated by a first valve, the controlled vacuum level may be applied to the surgical probe through a second valve connecting the probe to the small container volume. Whenever the controlled vacuum is shut off to the probe by the second valve, the first valve is opened to permit the fixed vacuum in the larger container to be applied to the smaller container to transfer aspirant fluid therein to the larger container by vacuum induction. In addition, a liquid level sensor in the small container is connected to trigger emptying of the small container whenever a preset liquid level is reached. Thus the smaller container is not permitted to fill completely, and the small volume thereof provides a minimal time lag in delivering the desired vacuum level to the surgical instrument or probe.

Each of the valves comprises a generally cylindrical valve chamber formed in the first wall assembly, with one flow port extending generally axially into the chamber and the other spaced laterally therefrom. An elastic membrane is clamped under tension across the valve chamber, extending generally perpendicularly to the axis of the chamber. A piston is received in the cylindrical chamber and disposed to impinge on the outer surface of the membrane, with a plunger extending from the piston outwardly of the wall assembly. Depression of the plunger drives the membrane to impinge upon the axially disposed port, thus interrupting the flow path between the two ports. The elastic nature of the membrane acts to bias the piston to the normally open position in which the flow path is maintained.

In a second preferred embodiment of the invention, the fast response, tubeless vacuum aspiration collection cassette includes one fluid collection container. Communication with a controlled variable vacuum source in the surgical aspiration machine and the conduit extending to the surgical probe or cutting instrument are substantially similar to those discussed with regard to the first preferred embodiment. A first wall portion of the cassette housing abutting the machine includes a connector positioned to engage a port in the machine to provide a controlled variable vacuum level to the container through a flow channel. A second flow channel extends to a port which is in communication with the connector adapted to be connected to a tubular conduit extending to a surgical probe or cutting instrument. A valve formed in the first wall portion is interposed in the second flow channel and has an actuating stem extending from the wall and positioned to be actuated selectively by appropriate components of the machine.

An additional feature of the second preferred embodiment includes input and output ports for attachment to a fluid infusion source and fluid infusion tool respectively. The input and output ports are formed within the first wall portion and are interconnected by a flow channel substantially the same as the other flow channels. Another valve is interposed in the flow channel and allows selective flow of infusion fluid between the fluid infusion source and tool.

The valves of the second preferred embodiment are substantially similar to those described with respect to the first preferred embodiment of the invention, and operate in conjunction with an elastic membrane clamped under tension across the valve chambers.

DESCRIPTION OF THE PREFERRED EMBODIMENT

The present invention generally comprises a device for collecting aspirant fluid from a vacuum aspiration surgical instrument or probe. It can optionally also control delivery of infusion fluid to an infusion surgical instrument or probe. One salient feature of the invention is that the device includes a cassette configuration which releasably engages the surgical instrument operating machine by simple plug insertion, thereby making all the required connections with the machine. Also, the cassette includes therein all the valves necessary to control the vacuum aspiration or infusion fluid functions, thus obviating the prior art problems associated with tubing connections, pinch valves, and the like. Moreover, the invention exhibits extremely fast response time in shifting the vacuum induction level, while also providing a large storage capacity for aspirant fluid and tissue debris. Other features of the invention will be apparent in the following description.

Figure 1:
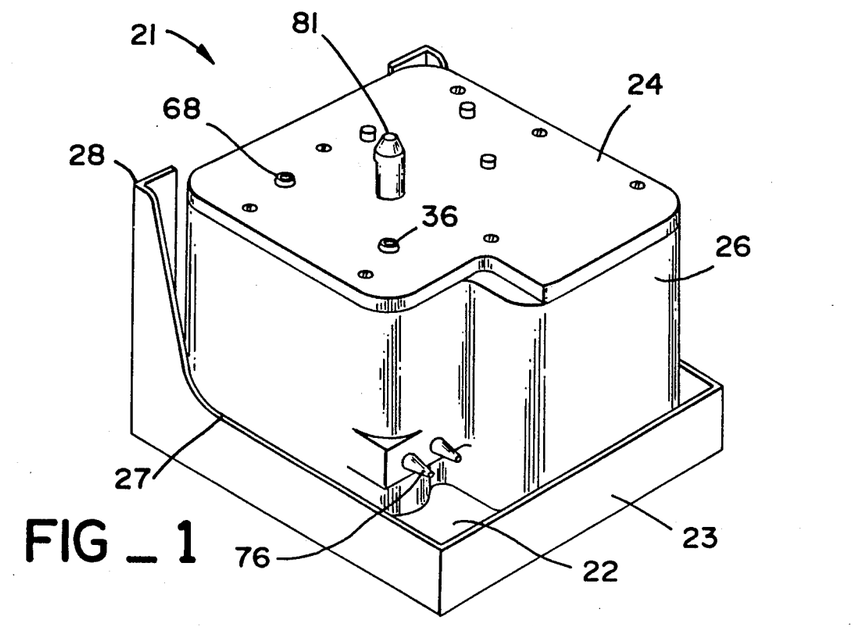
FIG. 1 is a perspective view of the aspiration cassette assembly of a first preferred embodiment of the present invention.
Figure 2:
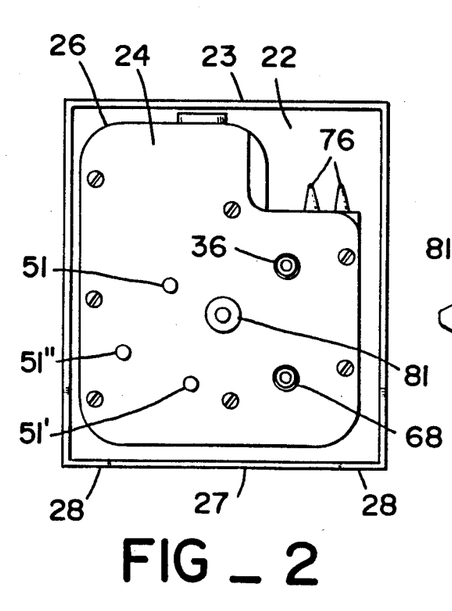
FIG. 2 is a rear view of the aspiration cassette assembly depicted in FIG. 1.
Figure 3:
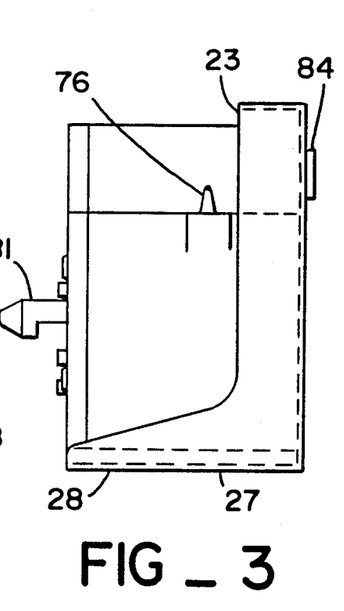
FIG. 3 is a side view of the aspiration cassette assembly depicted in FIGS. 1 and 2.

A first preferred embodiment of the invention is shown in FIGS. 1-18, and will be described as follows. With regard to FIGS. 1-3, the cassette 21 of the present invention includes an outer end wall 22 which is generally rectangular in configuration, with a narrow frame 23 extending about the periphery of the wall 22. An inner end wall 24 is parallel and spaced apart from the wall 22, and is provided with a smaller profile, slightly irregular rectangular configuration. A sidewall 26 extends continuously between the two end walls to define an enclosed volume therewith. The sidewall and end walls are preferably formed of molded polymer material, and are joined by adhesive means or ultrasonic welding to form a sealed unit. At the lower portion of the cassette, the frame 23 includes a portion 28 which flares to extend from the outer end wall to the inner end wall, adjacent to the opposed corners of the lower edge 27 of the wall 22.

Figure 4:
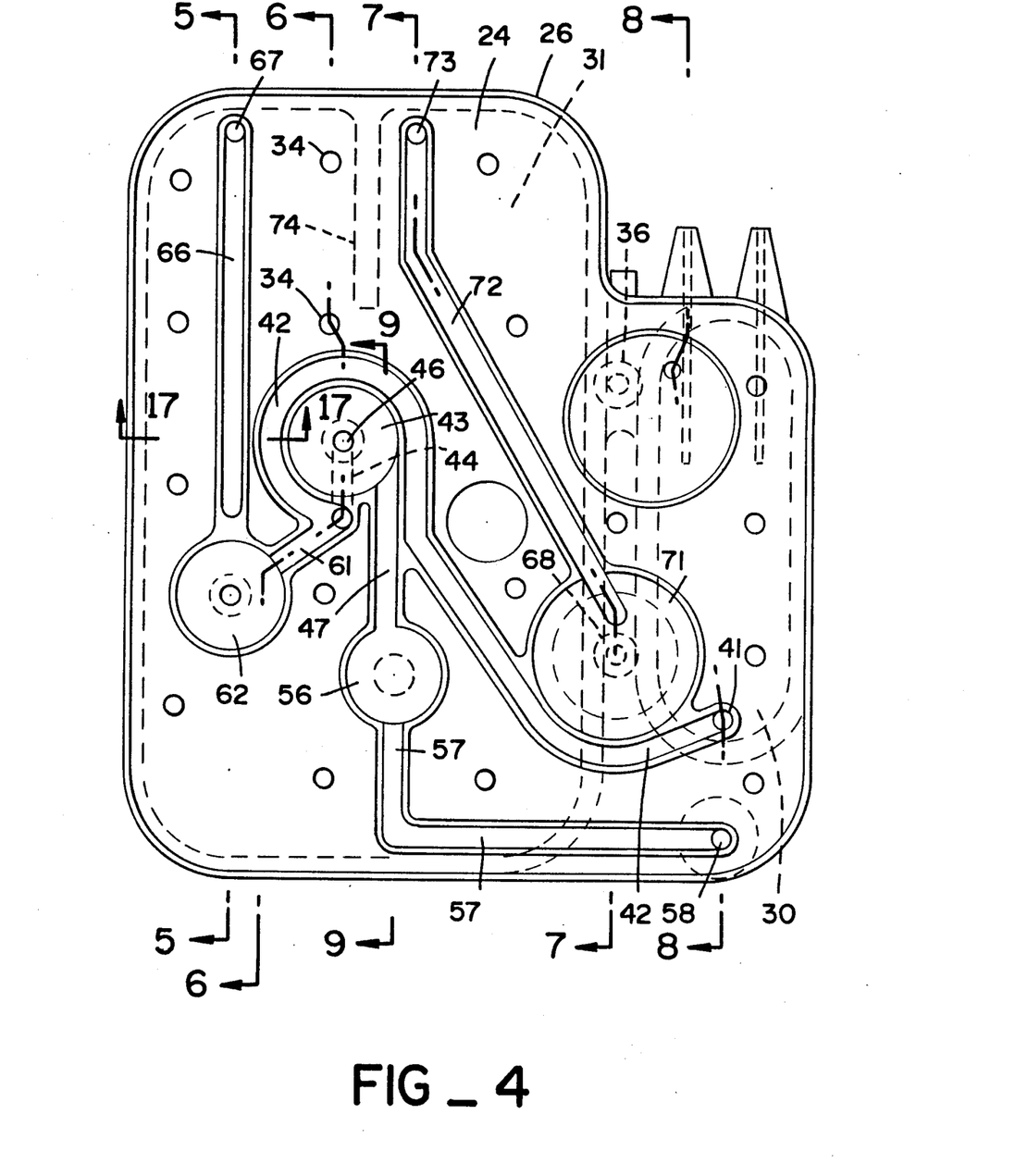
FIG. 4 is a plan view of the rear panel layout of the aspiration cassette assembly of FIG. 1.
Figure 8:
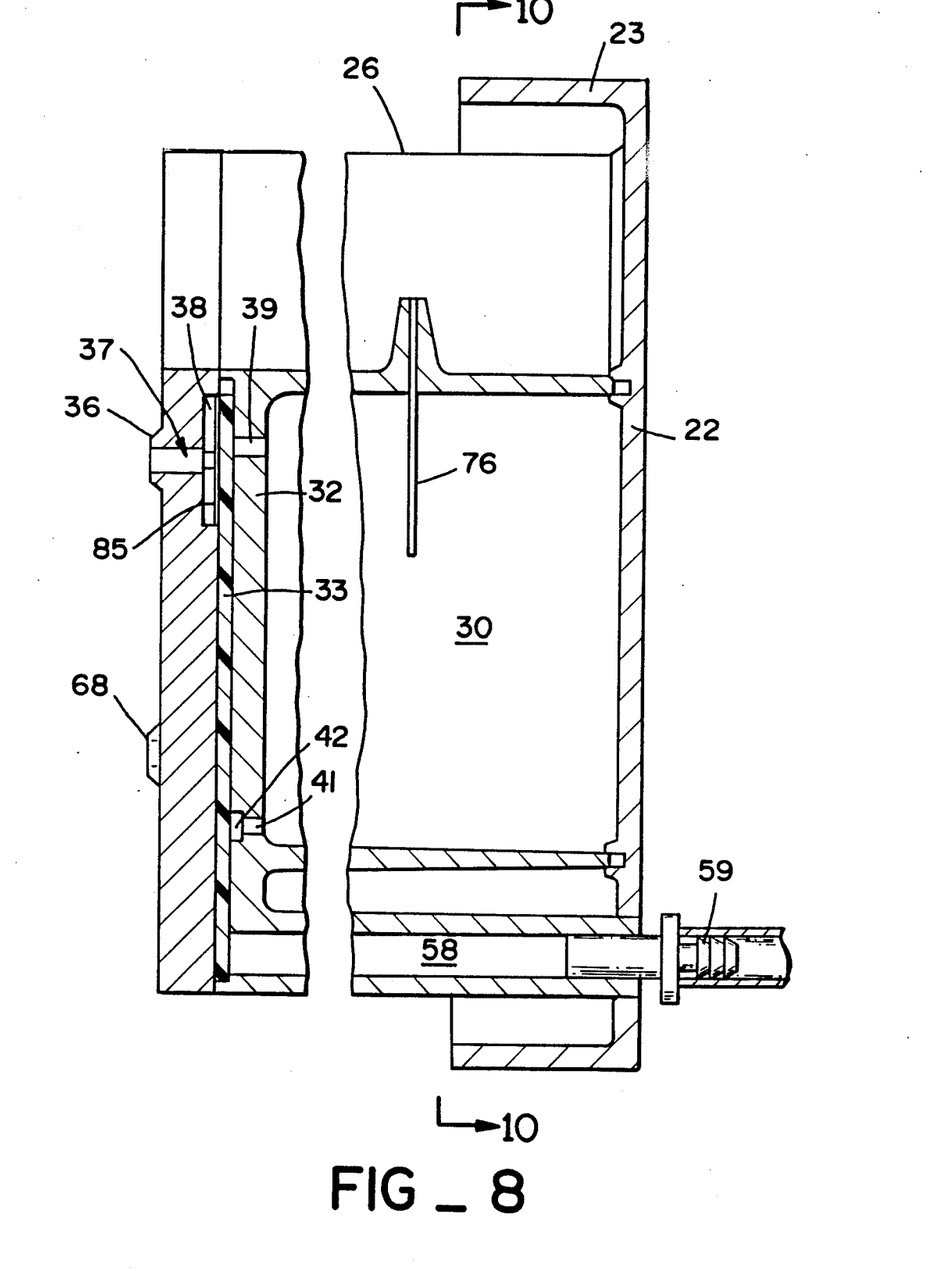
FIG. 8 is a cross-sectional elevation of the rear panel assembly of the cassette assembly, taken along line 8—8 of FIG. 4.
Figures 9, 10, 11, 12:
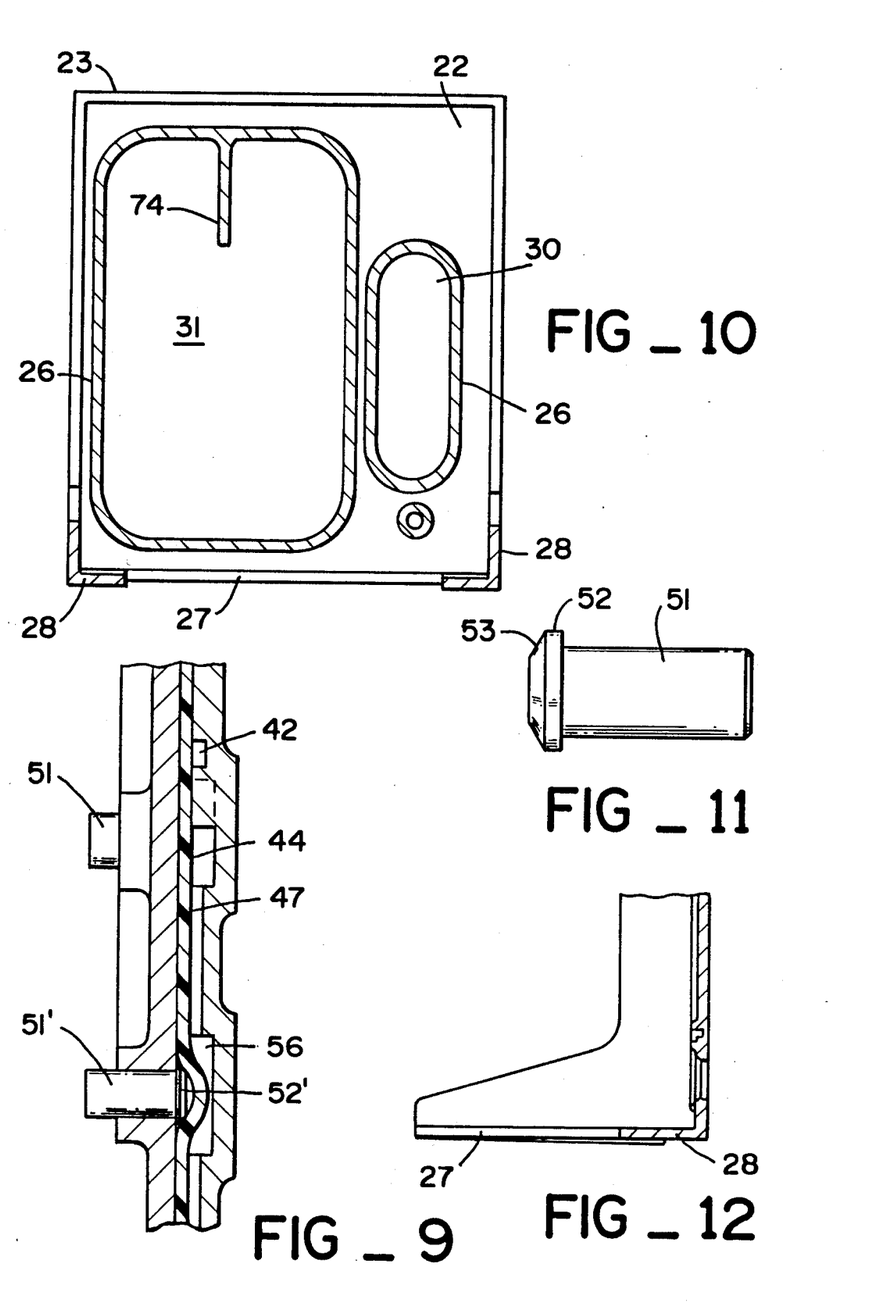
FIG. 9 is a partial cross-sectional elevation of the rear panel assembly of the cassette assembly, taken along line 9—9 of FIG. 4.
FIG. 10 is a cross-sectional view of the cassette assembly, taken along line 10—10 of FIG. 8.
FIG. 11 is a plan view of the valve stem and piston assembly of the present invention.
FIG. 12 is a partially cross-sectioned detail view of the corner assembly of the present invention.
Figure 13:
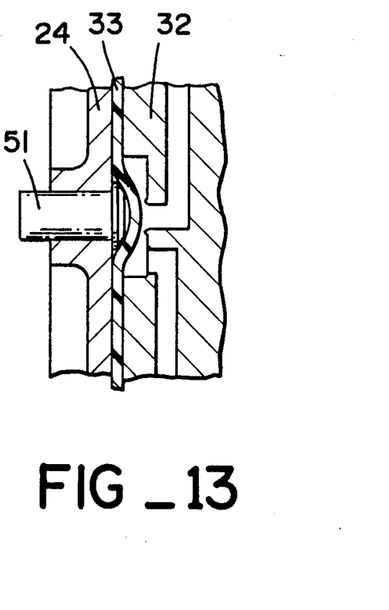
FIG. 13 is an enlarged, cross-sectional view of the valve assembly according to the present invention of FIG. 1.
Figure 14:
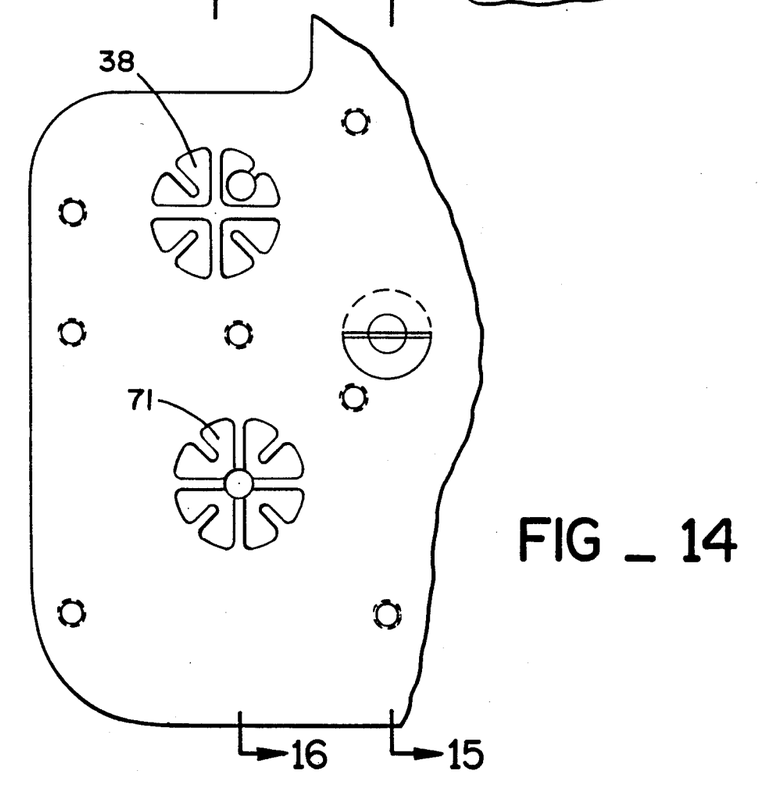
FIG. 14 is a partial plan view of the rear wall of the aspiration cassette of FIG. 1.
Figure 15:
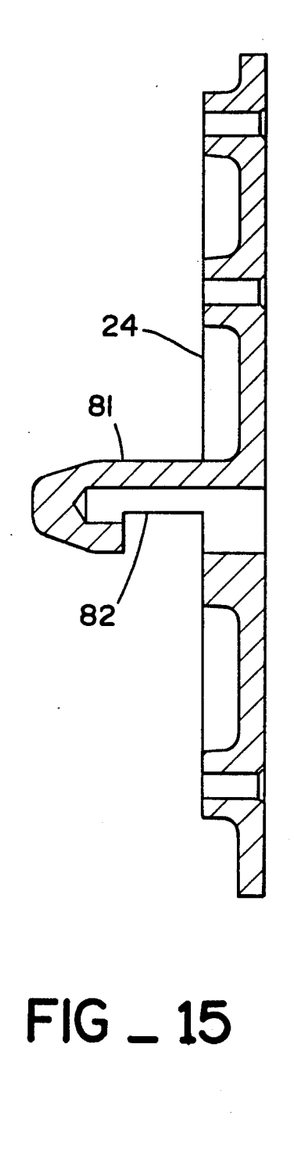
FIG. 15 is a cross-sectional elevation taken along line 15—15 of FIG. 14.
Figure 16:
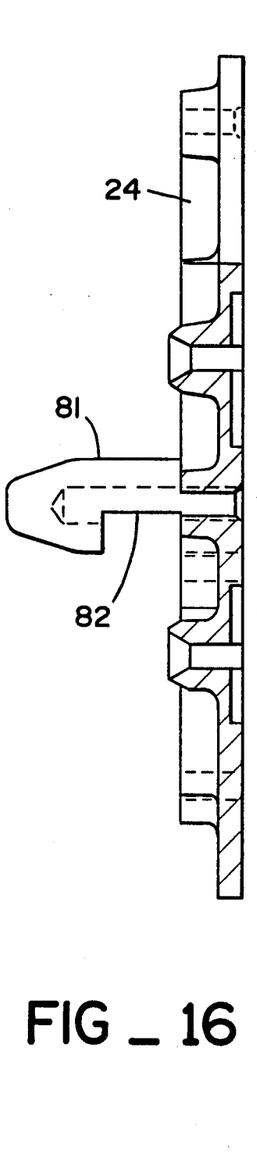
FIG. 16 is a cross-sectional elevation taken along line 16—16 of FIG. 14.

With regard to FIGS. 4, 8, and 10, the cassette 21 is provided with interior walls which define, together with the outer sidewalls 26, a pair of sealed containers 30 and 31. It is significant that the container 30 is small in volume, and that the container 31 is substantially larger. A system of flow channels and valves, formed by an assembly with the end wall 24, selectively connected the two containers. In addition, the smaller container 30 is connected to a controlled, variable vacuum source, and this source of vacuum is connected through the smaller container 30 to a surgical instrument or probe to aspirate fluid and tissue therefrom into the smaller container. It may be appreciated that the small volume of the container 30 closely follows the vacuum level of the source connected to it, so that the vacuum aspiration demanded by the surgeon is delivered to the surgical tool with virtually no perceptible time lag. Also, the system connects the larger container 31 to a fixed vacuum source and selectively to the smaller container, so that the smaller container may be emptied whenever it becomes full, or whenever the operation of the surgical instrument is halted even momentarily.

Joined to the end wall 24 is an inner panel 32 disposed parallel thereto and having the same general outer profile. A gasket member 33 is also provided with the same general outer profile, and is secured compressively between the wall 24 and the panel 32. The gasket 33 is formed of a resilient, inert material, such as silicone rubber or the like. A plurality of locating pins 34 extend from the inner panel 32 through appropriately placed holes in the gasket to be received in friction fit in apertures in the end wall 24. The pins 34 facilitate assembly of the device in a precision manner, and the gasket provides a pressure-tight vacuum seal. In addition, the inner panel 32 includes flow channels and valve chambers formed integrally therein during the molding process, so that the end wall 24 together with the inner panel and the gasket define all the required valves and flow channels.

Extending distally from the end wall 24 is a vacuum connector nipple 36, as shown in FIG. 8. The nipple 36 is disposed to be engaged by the surgical instrument control machine, and a passage 37 leads therefrom through the end wall 24 to a filter well 38. A hydrophobic filter membrane 85 is received in the well 38, and is clamped at its outer edge between the end wall 24 and the gasket 33. From the filter well 38 a passage 39 in the inner panel 32 leads directly to the sealed volume of the small container 30. The connector 36 receives the controlled, variable vacuum from the surgical machine, and transfers this vacuum directly to the small container 30.

Figures 5, 6, 7:
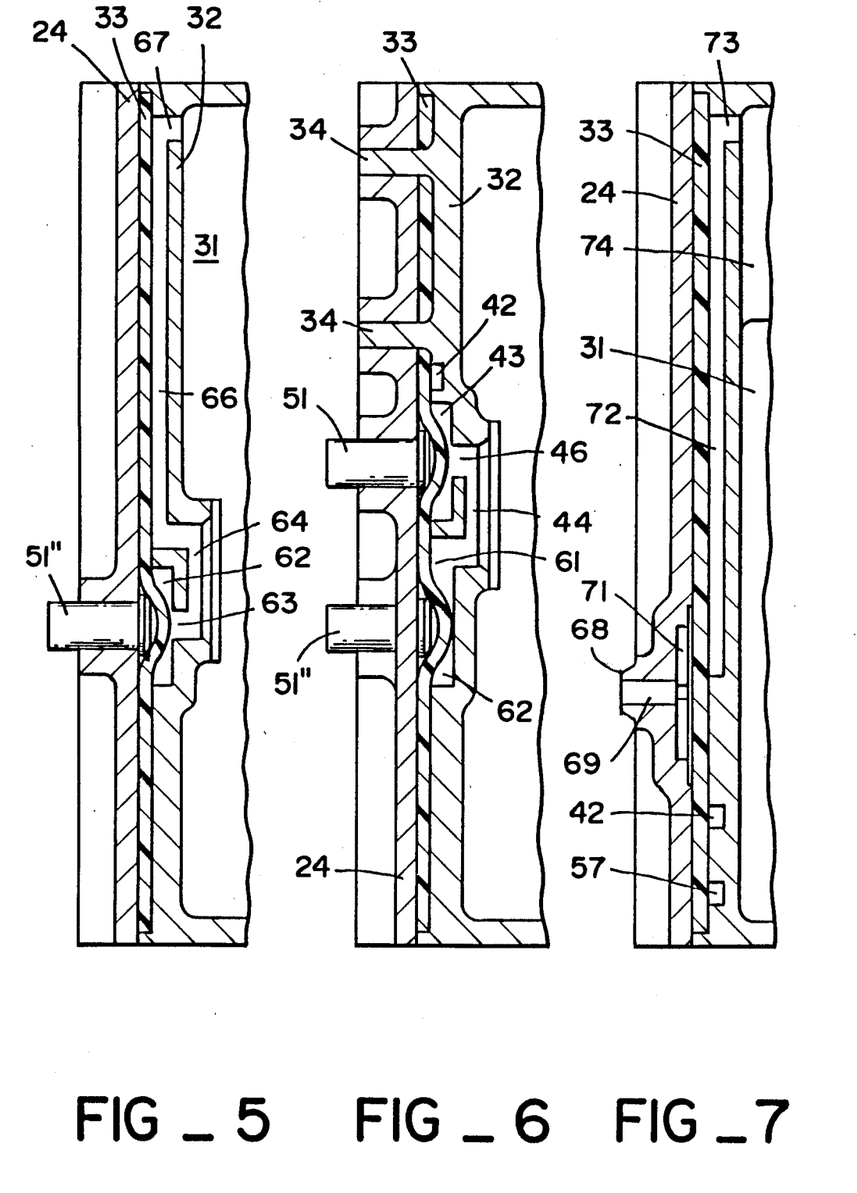
FIG. 5 is a cross-sectional elevation of the rear panel assembly, taken along line 5—5 of FIG. 4.
FIG. 6 is a cross-sectional elevation of the rear panel assembly, taken along line 6—6 of FIG. 4.
FIG. 7 is a cross-sectional elevation of the rear panel assembly, taken along line 7—7 of FIG. 4.

A port 41 in the lower end of the container 30 extends to a flow channel 42 formed in the panel 32, as shown in FIGS. 4 and 8. The flow channel 42 extends obliquely to the vicinity of a valve chamber 43, which comprises a cylindrical cavity formed in the inner panel 32. The channel 42 extends about the periphery of the valve chamber 43 for more than half the circumference thereof, and joins a recessed flow passage 44, as also shown in FIG. 6. The passage 44 leads to a port 46 extending axially into the valve chamber 43. A flow channel 47 extends in the inner panel 32 to join the valve chamber 43 and the cylindrical chamber 56 in a tangential relationship, as also shown in FIGS. 4 and 9.

A valve stem actuator 51 extends outwardly through a hole in the end wall 24, and is joined at the inner end of a piston head 52, as also shown in FIGS. 6 and 11. The inner end of the piston head has a chamfered portion 53 to present a smoothly contoured surface to impinge upon the gasket 33. The head 52 is smaller in diameter than the valve chamber, and the stem 51 is aligned axially therewith. It may be appreciated that inward translation of the stem 51 drives the head 52 to deform the gasket 33 elastically, urging the gasket material to block the port 46 and prevent fluid flow through the valve chamber. See also FIG. 13. The elastic nature of the gasket material opposes the inward translation of the valve stem, and assures that the valve will be biased to the normally open position to restore fluid flow when the valve stem is released. The valve stem is actuated by a mechanism of the surgical instrument operating machine, which forms no part of the present invention.

The flow channel 47 leads to a cylindrical chamber 56 similar in configuration to the valve chamber 43. Another flow channel 57 extends from the chamber 56, and leads to a delivery tube 58 which extends to the outer end wall 22 (FIG. 8). A tubing nipple 59 may be mounted on the outer end of the delivery tube 58 to connect to the aspiration tube of a surgical instrument or probe. The flow channels 47 and 57 enter the chamber 56 in diametrically opposed relationship.

A valve stem 51 extends through the end wall 24, and functions as its counterpart 51 to deform the gasket portion upon which it impinges and urge that portion into the chamber 56, as shown in FIG. 9. However, the gasket portion in the chamber 56 does not block the fluid flow therethrough, due to the diametrical relationship of the flow channels entering therein. Rather, the piston 52 is provided to create a back pressure wave, or reflux, whenever the vacuum delivered to the surgical instrument is shut off by the valve 43.

To summarize the function of the components described thus far, the controlled variable vacuum provided to the small container 30 by the connector 36 is delivered through the channel 42, valve 43, chamber 56, channel 57, and delivery tube 58 to the aspirating surgical instrument. When the surgeon desires to cease the cutting action of the instrument, a hand or foot control is actuated to activate the valve stem 51 and close the valve 43. Thus any further vacuum induction of tissue into the surgical instrument is stopped abruptly. However, a vacuum condition may remain in the fluid channel extending from the valve 43 to the surgical instrument. This residual vacuum may act to retain tissue in the cutting instrument; when the surgeon withdraws the instrument from the surgical site, the tissue may be torn or damaged. This effect can be especially serious in delicate eye surgery and the like.

Thus, the reflux action of the chamber 56 is an important feature of the present invention in preventing such accidental damage. Whenever the valve 43 is closed to stop the vacuum aspiration, the valve stem 51 is actuated to drive the gasket 33 into the chamber 56, thereby displacing a small amount of the fluid in the chamber into the fluid flow path from the surgical instrument to the valve 43. The result is that the residual vacuum is alleviated, and any tissue retained in the cutting instrument is released.

The distal end of the arcuate portion of the flow channel 43 is also connected through a short channel portion 61 to a valve chamber 62. The valve chamber 62 is configured similarly to the chamber 43, and a valve stem actuator 51 is translatably secured in the end wall 24 and disposed to function like its counterpart 51 described previously. The axially disposed port 63 of the chamber 62 connects to a recessed flow channel 64, and thence to a flow channel 66, as shown in FIGS. 4 and 5. The flow channel 66 terminates in a port 67 which opens into the large container 31. Thus a fluid flow path from the small container to the large container is defined through channels 42 and 61, valve chamber 62, channels 64 and 66, and port 67, with the valve 62 being interposed to selectively block the flow path.

Also extending outwardly from the end wall 24 is another vacuum connector nipple 68. Like the connector 36, the connector 68 is positioned to be connected with a port in the surgical machine, and is provided with a generally constant vacuum by the machine. The connector 68 is joined by a passage 69 to a filter well 71 which is also covered by a hydrophobic membrane 85, and thence through a flow channel 72 to a port 73 in the large container 31 (FIGS. 4 and 7). Thus the constant vacuum applied to the connector 68 is delivered directly to the large container 31. It should be noted that the container 31 includes a septum wall 74 which separates the vacuum port 73 and the fluid intake port 67, so that no fluid inadvertently enters the port 73. Also, the hydrophobic membrane permits gas flow into the surgical machine, but prevents aspiration of any liquid into the surgical machine.

To summarize the operation of the cassette of the first preferred embodiment of the present invention, the controlled, varible vacuum level of the surgical machine is applied to the connector 36 and conducted directly to the small volume of the container 30. To provide vacuum aspiration to a surgical instrument connected to the nipple 59, the valve 43 is open to permit vacuum connection from the small container through flow channel 42, valve 43, channels 47 and 57 to the delivery tube connected to the instrument. At the same time the valve 62 is closed, thus isolating the large and small containers.

Whenever the surgeon desires to curtail the vacuum aspiration effect, even momentarily, the surgeon's controller activates the machine to close valve 43, thus interrupting the aspiration flow path to the surgical instrument. At the same time, the valve stem 51 is actuated to displace fluid in the aspiration channel and alleviate the residual vacuum therein to release any tissue entrained in the surgical cutting instrument. Also at the same time, the valve 62 is opened, thus connecting the two containers through the channels 42 and 47, the valve 62, and the channel 66. The vacuum level constantly applied to the connector 68 causes any fluid above the port 41 of the small container to be drawn rapidly into the large container through the open flow channel just described, thus emptying the small container.

The small container also includes a pair of electrodes 76 which extend into the upper portion of the small container and are connected to a circuit in the surgical machine which senses fluid immersing the two electrodes. Whenever fluid bridges the two electrodes 76, the machine temporarily disables the surgical instrument, closes valve 43, actuates the reflux device 56, and opens the valve 62 to drain the small container. This process requires a very brief time to complete, and assures that the small container will not fill to the level of the port 39, thus preventing fluid aspiration into the surgical machine.

Figure 17:
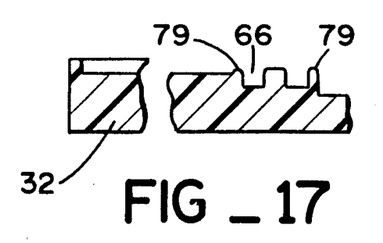
FIG. 17 is an enlarged, detailed cross-sectional view taken along line 17—17 of FIG. 4.
Figure 18:
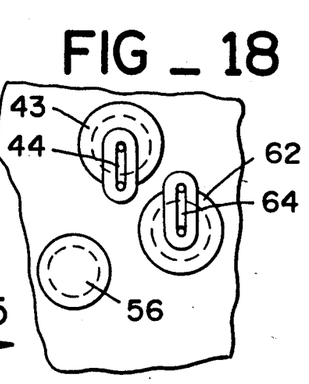
FIG. 18 is a detailed plan view of the valve construction of the present invention of FIG. 1.

With regard to FIG. 17, it should be noted that all of the flow channel and valve chamber features described herein include a raised lip 79 extending continuously from the inner panel 32 and impinging on the gasket 33. The lip assures a vacuum-tight seal with the gasket, and is integrally molded with the panel 32.

The cassette 21 also includes a pilot pin 81 extending outwardly from the end wall 24, as shown in FIGS. 1-3 and 15-16. The pilot pin is disposed to be received by a complementary part of the surgical machine, and is provided to guide and secure the engagement of the connectors 36 and 68 with the machine. The pin 81 includes a detent slot 82 spaced proximally from the end thereof and adapted to be engaged by a latch mechanism of the surgical machine to secure the cassette to the machine in the operative position.

The cassette of the present invention is easily formed by plastic molding techniques, and may be manufactured inexpensively. Thus the cassette is suitable for single usage, and disposal thereafter. A plugged port 84 extending through outer wall 22 to the large container 31 is provided so that the aspirant fluid and tissue debris may be withdrawn for pathology analysis and the like.

Although the tubeless vacuum aspiration collection cassette of the present invention has been described above in connection with a preferred embodiment in which a pair of containers is utilized, it will be appreciated by those skilled in the art that the flow passage means, valve means, valve actuator means, and other important features of the present invention are adaptable for use in cassettes which utilize either a single container or more than two containers.

It is also to be appreciated by those skilled in the art that the flow passage means, valve means, valve actuator means, and other important features of the present invention are adaptable for use in cassettes for the selective control of fluids, in addition to air under vacuum, which are used in surgical procedures. Such examples include, but are not limited to, infusion fluid and pressurized air.

A second preferred embodiment of the present invention is therefore shown in FIGS. 19-24, and described as follows.

Figure 19:
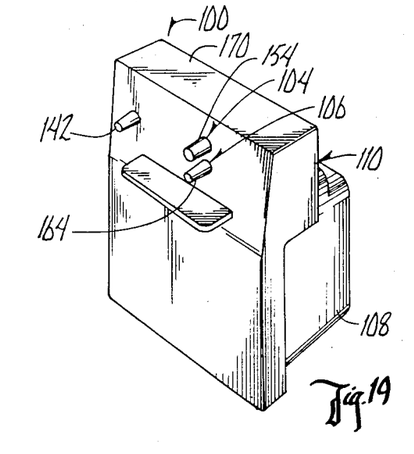
FIG. 19 is a perspective view of a second preferred embodiment of the present invention.
Figure 20:
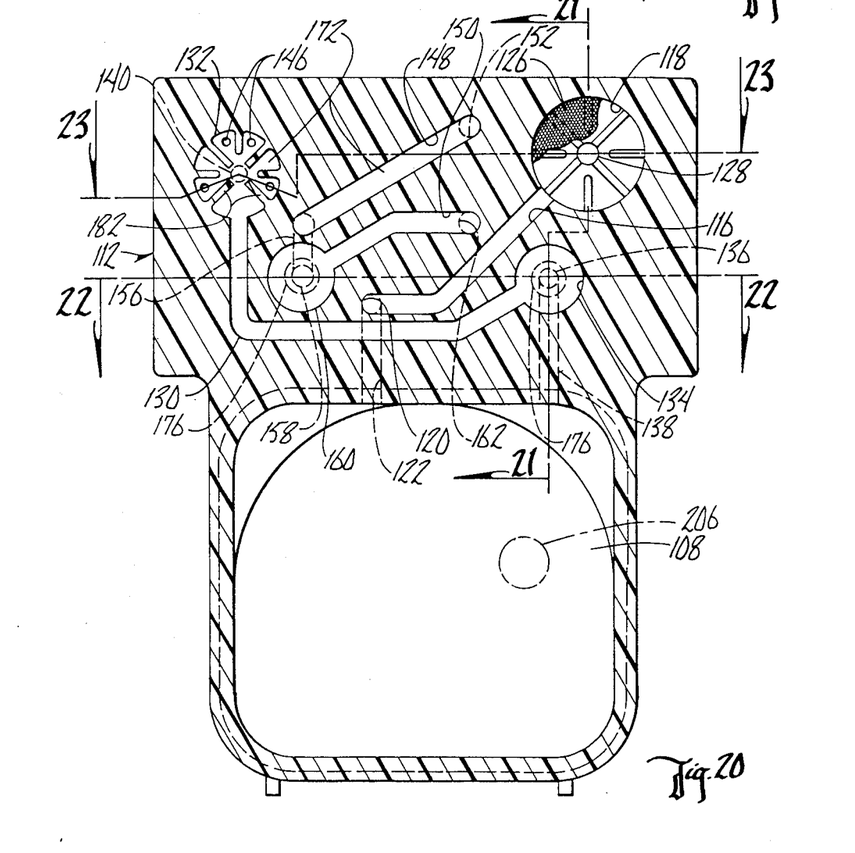
FIG. 20 is a cross-sectional elevation taken along lines 20—20 of FIG. 21.
Figure 21:
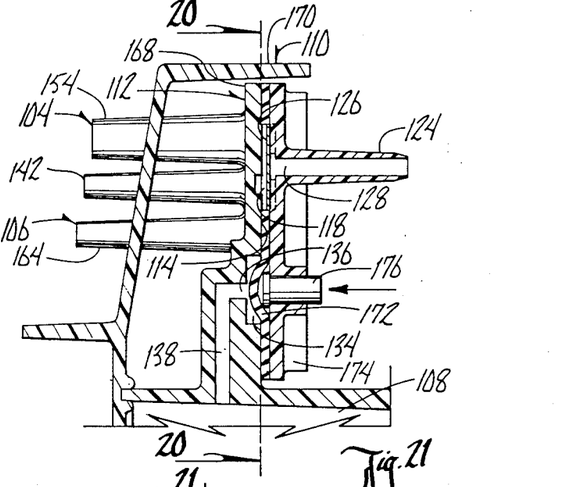
FIG. 21 is a side cross-sectional elevation taken along line 21—21 of FIG. 19.

With particular reference to FIGS. 19-21, the second preferred embodiment of the present invention comprises a cassette 100 substantially similar in design and operation to cassette 21 of FIGS. 1-18. A pilot pin 102 (see FIGS. 22 and 23), like pilot pin 81 of the first preferred embodiment, locks cassette 100 to the surgical machine.

Cassette 100, like cassette 21, can be connected to tubing conduit extending to a surgical aspiration tool, and is also connectable to an aspiration source in the surgical machine. Flow passage means, valve means, and valve actuator means, substantially the same as with regard to the first preferred embodiment, allow control of direction of aspiration to the aspiration tool the control and direction of aspiration fluid and depris to a collection container 108 disposed within cassette 100.

Cassette 100 also includes the additional optional feature of allowing selective control of infusion fluid between an infusion fluid source and conduit tubing to an infusion fluid surgical tool. Cassette 100 includes an infusion fluid inlet 104 and an infusion fluid outlet 106 connectible to an infusion fluid source and tool respectively. Flow passage means, valve means, valve actuator means, substantially similar to those shown in and described with regard to the first preferred embodiment of the present invention, are utilized to control infusion fluid to the infusion fluid surgical tool.

It is to be understood that the elements and operation of cassette 100 function substantially in the same way as described with regard to the first preferred embodiment of the present invention, and therefore reference should be had to that description and will not be repeated herein.

The primary differences between cassette 100 and cassette 21 are summarized as follows. As shown in FIG. 20, a single fluid collection container 108 is disposed within cassette housing 110. A first wall portion 112 of cassette housing 110 extends above container 108. As is most clearly shown in FIG. 20, a plurality of fluid flow channels are formed in the machine-facing surface 114 of wall portion 112. A first flow channel 116 connects circular filter well 118 to a port 120. Port 120 is in turn in communication with bore 122 which is in turn is in communication with the interior of container 108. As shown in FIG. 21, a connecting nipple 124 is in fluid communication with circular filter well 118 containing a hydrophobic filter membrane 126. Nipple 124 automatically connects to the aspiration source of the machine when cassette 100 is connected and secured to the machine. First flow channel 116, port 120, and bore 122, in conjunction with filter well 118 and port 128 associated with connecting nipple 124 therefore supply aspirating vacuum to container 108.

A second flow channel 130 in first wall portion 112 extends between segmented well 132 and valve chamber 134 which surrounds port 136. Port 136 in turn is in fluid communication with bore 138 which fluidly communicates with container 108. Segmented well 132 is in fluid communication with port 140 which is associated with aspiration tool nipple 142. The fluid pathway through segmented well 132, second flow channel 130, and bore 138 provides a pathway for fluid and debris aspirated from the surgical aspiration tool into the collection container 108. Valve chamber 134 cooperates with gasket member 172 and valve stem 176, in the same way as previously described with regard to the first preferred embodiment, to allow closing and opening of this fluid pathway.

A third flow channel 148 and fourth flow channel 150 are formed in first wall portion 112. Third flow channel 148 at one end communicates with port 152 which in turn communicates with infusion fluid input nipple 154. The other end of third flow channel 148 communicates with recessed flow channel 156 which in turn communicates with port 158 in the center of valve chamber 160. Fourth flow channel 150 communicates at one end with port 162 which in turn communicates with infusion fluid outlet nipple 164. The other end of fourth flow channel 150 communicates directly with valve chamber 160. Valve chamber 160, like valve chamber 134 and those described with regard to the first preferred embodiment of the invention cooperate with gasket 172 and valve stem 176 to selectively block port 158 and stop fluid flow between third and fourth flow channels 148 and 150. Thus, the surgical machine can also control infusion fluid to an infusion fluid tool.

Figures 22, 23, 24, 25:
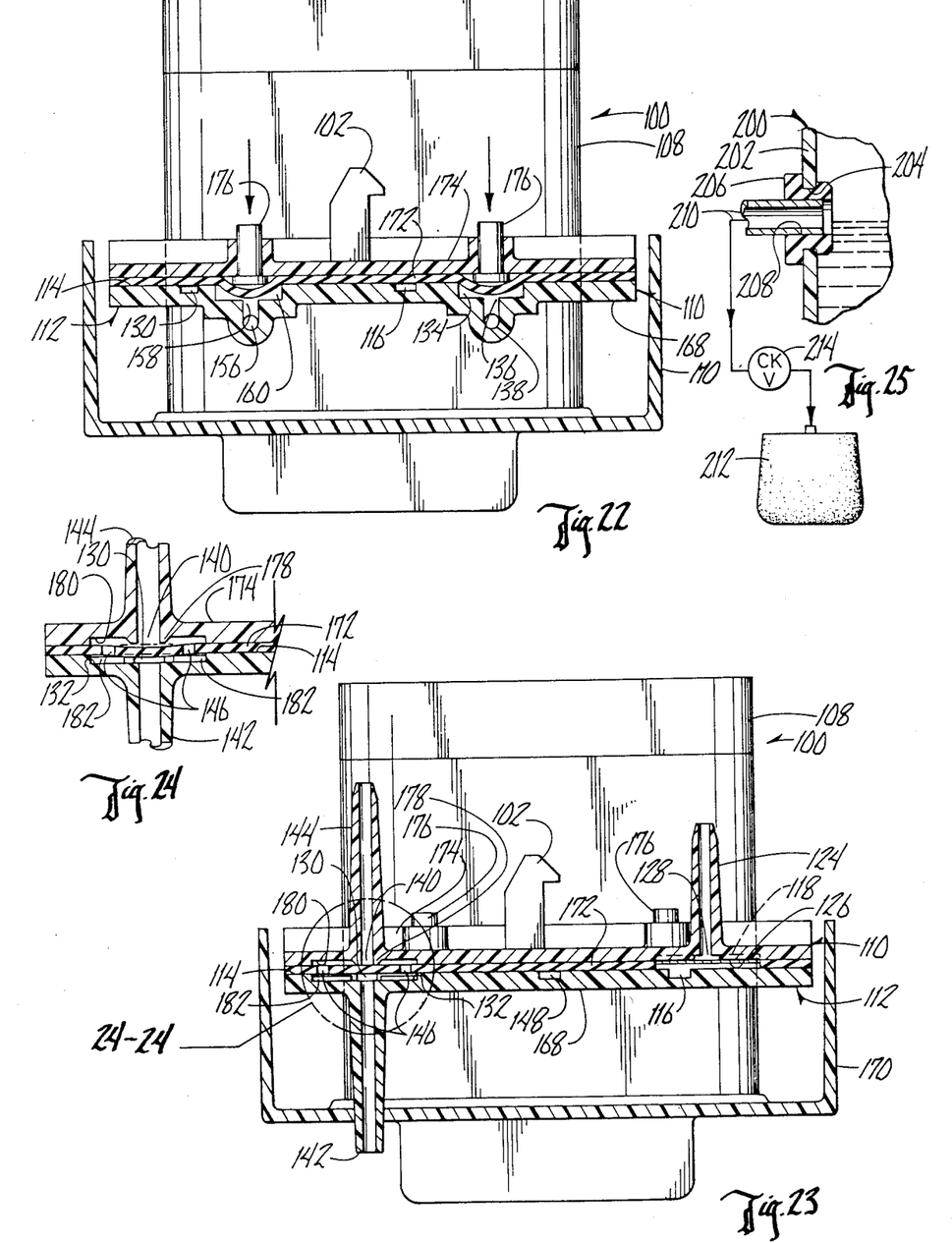
FIG. 22 is a top cross-sectional view taken along line 22—22 of FIG. 20.
FIG. 23 is a top cross-sectional view taken along line 23—23 of FIG. 20.
FIG. 24 is an enlarged, cross-sectional view of the vent assembly according to the present invention of FIG. 19, showing venting in operation.
FIG. 25 is a schematic representation of an optional auxiliary fluid container system which can be used with the present invention.

Aspiration tool nipple 142, infusion fluid input nipple 154, and infusion fluid outlet nipple 164 extend from the surface 168 of wall portion 112 which faces away from the surgical machine. They extend through appropriate aperatures in a manifold hood 170 which extends up and over first wall portion 112. Hoses or tubing conduit, as appropriate are connected to the nipples as desired. FIGS. 21–23 shown how gasket membrane 172 is sandwiched over the flow channels wells, and valve chambers in first wall portion 112 by a backplate 174. Backplate 174 can be secured to first wall portion 112 similarly to that described with regard to the first preferred embodiment of the invention.

It is also to be understood that the second preferred embodiment includes a vent and check valve to vent the aspiration line to the surgical aspiration tool to atmosphere. By referring to FIGS. 20, 23, and 24, the check valve and vent can be described. A vent nipple 144 surrounds a port 140 and extends outwardly from back plate 174. Vent nipple 144 connects with a venting valve in the machine when cassette 100 is secured in the machine. The venting valve is connected to atmosphere, is controlled by the machine, and operates as is known in the art.

Port 140 has a raised lip 178 surrounding it, which in turn is surrounded by a well 180. As can be seen in FIGS. 23 and 24, port 140, lip 178, and well 180 align with segmented well 132 in first wall portion 112, but are separated from it by gasket 172. Although small apertures 146 exist in gasket 172, fluid and debris traveling through aspiration nipple 142 into second flow channel 130, and on to container 108, can not enter vent nipple 144 because when the venting valve in the machine is closed, gasket 172, in its normal state, covers and seals over raised lip 178 around port 140. The positioning of the four small apertures 146 can be seen in FIG. 20. It is also pointed out that spoke members 182, which extend from first wall portion 112 into segmented well 132, keep gasket 172 from blocking the flow path through aspiration 142.

FIG. 24 shows that when aspiration is stopped to the aspiration tool, and the venting valve in the machine is opened, the atmospheric pressure causes gasket 172 to move away from lip 178 and the aspiration line is vented to atmosphere through small apertures 146. This assists in diminishing residual vacuum in the aspiration line.

FIG. 25 shows an additional modification which can be made to the cassettes of the invention to provide auxilliary storage of fluid or debris aspirated into the collection container, such as container 31 of the first described preferred embodiment, or container 108 of the second described preferred embodiment. FIG. 25 shows a cassette 200 in accordance with the present invention with a fluid container 202 disposed therein. An aperture 204 is in fluid communication with the interior of container 202. It is preferred that aperture 204 be at least $\frac{1}{2}$" below the top of container 202. A plug 206 is sealingly positioned in aperture 204, but also has an aperture 208 into which a tube 210 is sealingly mounted. The opposite end of tube 210 is connected in fluid communication with sealed auxillary bag 212. A check valve 214 is interposed along tube 210. Check valve 214 allows fluid and debris to drain from container 202 to bag 212 when the level of fluid and debris in container 202 reaches aperture 208 in plug 206. Such drainage is by gravity. Check valve 214 disallows, however, passage of fluid, debris, or air from bag 212 back to container 202 when container 202 is under vacuum.

Such check valves are well-known to those of ordinary skill in the art and can take on various configurations while accomplishing the objects above described. An example is a diaphram check valve which allows fluid flow in one direction, but disallows it in another. A further example is a duckbill check valve. Other types could be used as is known in the art.

The auxilliary storage system described above is particularly useful in phaco-emulsification ophthalmic procedures, but is applicable to most, if not all, ophthalmic procedures.

It will be appreciated that the present invention can take many forms and embodiments. The true essence and spirit of this invention are defined in the appended claims, and it is not intended that the embodiments of the invention presented herein should limit the scope thereof.

What is claimed is:

1. A fast response vacuum aspiration system for use with a source of aspiration and an aspiration surgical instrument comprising:
   a removable cassette housing which includes a wall portion, having a first surface which, when in use, is oriented towards said source of aspiration;
   at least one sealed collection container secured within said cassette housing;
   at least one flow channel formed in said first surface of said wall portion of said cassette housing for communicating said container with said source of vacuum and said aspiration tool;
   a resilient gasket means abutting said first surface of said wall portion and covering said fluid channels to seal said fluid channels;
   a retaining plate, associated with said cassette housing, sandwiching said gasket means to said wall portion;
   one or more valve seats interposed along said flow channel adapted to receive valve actuator means through said retaining plate to force a portion of said gasket means into said valve seat blocking any fluid flow in said flow channel; and
   each said valve seat connecting first and second portions of said flow channel and comprising a cavity positioned in the wall portion of the cassette housing and being defined by side walls and a bottom wall, and including an aperture in the bottom wall which is in fluid communication with the second portion of the fluid flow channel, said first portion of the flow channel entering said cavity at least partially through said side wall.

2. The system of claim 1 wherein the cavity communicates with the second portion of the flow channel through a passage between the aperture of the cavity and the second portion of the flow channel, whereby the second portion of the flow channel is above the passage.

3. The system of claim 2 wherein the bottom wall of the cavity generally is parallel with the wall portion, the side walls of the cavity having a lip extending above the surface of the wall portion and said passage generally being beneath and parallel to the bottom wall of the cavity.

4. The system of claim 1 wherein the retaining plate is secured to the housing with the gasket sandwiched in between by a plurality of posts extending outwardly and generally perpendicular to the wall portion, said gasket having apertures aligned with corresponding posts, said retaining plate having sockets aligned with and allowing for frictional fitting of the posts therein.

5. The system of claim 4 wherein said sockets include reinforcing structure formed on the opposite side of the retaining plate than that which abuts the gasket, said other side of the retaining plate being generally flat to present a uniform and rigid surface, uninterrupted except for the apertures, to produce sealing under positive and negative pressure.

6. The system of claim 5 wherein the reinforcing structure comprises protrusions through which wheel sockets extend, said wheel protrusions being linked by ribs to form a network of reinforcement.

7. The system of claim 1 wherein said gasket and retaining plate include one or more aligned apertures for communication of fluid flow from the machine to the cassette housing.

8. A fluid collection device for a vacuum aspiration machine, including:
   cassette housing means adapted for interconnection with the machine providing fluid aspiration by vacuum induction, said cassette housing means having a wall portion which includes a first surface facing said machine when said device is interconnected with said machine;
   enclosed container means within said cassette housing means for retaining fluid;
   first connection means on said device for connecting a vacuum aspirating tool to said device;
   second connection means associated with said wall portion of said cassette housing means for connecting said device to a source of vacuum provided by the machine; and
   first valve means interposed in first flow channel means integrally formed in said wall portion of said cassette housing means for selectively connecting said first connection means to said container means to deliver said vacuum from said container means to the vacuum aspirating tool;
   a plug means positioned in a wall of the container means for gaining access to the interior of the container means, said plug means including an aperture which is in fluid communication with the interior of the container means, and having a removable plug member for sealing closing of the aperture.

9. The device of claim 8 wherein said plug means includes a bore, a fluid conduit sealingly secured to the bore in the plug, said fluid conduit being in fluid communication between the interior of the container means and a supplemental fluid storage container.

10. The device of claim 9 wherein the supplemental fluid storage container comprises a bag means which is removable and sealable for storage and disposal of fluid.

11. A fluid collection device for a vacuum aspiration machine, including:
    cassette housing means adapted for interconnection with the machine providing fluid aspiration by vacuum induction, said cassette housing means having a wall portion which includes a first surface facing said machine when said device is interconnected with said machine;
    enclosed container means within said cassette housing means for retaining fluid;
    first connection means on said device for connecting a vacuum aspirating tool to said device;
    second connection means associated with said wall portion of said cassette housing means for connecting said device to a source of vacuum provided by the machine;
    first valve means interposed in first flow channel means integrally formed in said wall portion of said cassette housing means for selectively connecting said first connection means to said container means to deliver said vacuum from said container means to the vacuum aspirating tool; and
    a splash shield extending from an interior surface of the container inwardly between a fluid inlet and a vacuum opening in the container to prevent splashing of fluid into the vacuum opening.

* * * * *